(12) United States Patent
Loo et al.

(10) Patent No.: US 8,618,521 B2
(45) Date of Patent: Dec. 31, 2013

(54) PLURIDIRECTIONAL VERY HIGH ELECTRON ENERGY RADIATION THERAPY SYSTEMS AND PROCESSES

(71) Applicant: The Board of Trustees of the Leland Stanford Junior University, Palo Alto, CA (US)

(72) Inventors: Billy Wiseman Loo, Foster City, CA (US); Peter G. Maxim, Palo Alto, CA (US); Valery A. Dolgashev, San Carlos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/765,017

(22) Filed: Feb. 12, 2013

(65) Prior Publication Data

US 2013/0231516 A1     Sep. 5, 2013

Related U.S. Application Data (60) Provisional application No. 61/606,408, filed on Mar. 3, 2012.

(51) Int. Cl.
    *G21K 5/04*     (2006.01)

(52) U.S. Cl.
    USPC .......................... 250/492.3; 250/492.1; 600/1

(58) Field of Classification Search
    USPC ......... 250/492.1, 492.3, 423 R, 423 P; 600/1, 600/2, 3, 4, 5
    See application file for complete search history.

(56) References Cited

U.S. PATENT DOCUMENTS

| | | | |
|---|---|---|---|
| 3,757,118 A | 9/1973 | Hodge et al. | |
| 4,644,168 A | 2/1987 | Rand et al. | |
| 4,737,647 A | 4/1988 | Stieber | |
| 5,452,720 A * | 9/1995 | Smith et al. | 600/427 |
| 5,684,854 A | 11/1997 | Hughes | |
| 6,332,017 B1 | 12/2001 | Carroll et al. | |
| 6,333,966 B1 | 12/2001 | Schoen | |
| 6,459,762 B1 | 10/2002 | Wong et al. | |

(Continued)

OTHER PUBLICATIONS

Bazalova, M., et al., "WE-C-BRB-05: Monte Carlo Simulations and Experimental Validation of Rapid Dose Delivery with Very High-Energy Electron Beams"; and Papaconstadopoulos, P., et al., "WE-C-BRB-04: Fast and Accurate Hybrid Source Model for Modulated Electron Radiotherapy"; Medical Physics, vol. 39, No. 6, Jun. 2012, p. 3944.

(Continued)

*Primary Examiner* — Nicole Ippolito
(74) *Attorney, Agent, or Firm* — Kilpatrick Townsend & Stockton LLP; Kenneth R. Shurtz, Esq.; James L. Ewing IV, Esq.

(57) ABSTRACT

A compact high-gradient, very high energy electron (VHEE) accelerator and delivery system (and related processes) capable of treating patients from multiple beam directions with great speed, using all-electromagnetic or radiofrequency deflection steering is provided, that can deliver an entire dose or fraction of high-dose radiation therapy sufficiently fast to freeze physiologic motion, yet with a better degree of dose conformity or sculpting than conventional photon therapy. In addition to the unique physical advantages of extremely rapid radiation delivery, there may also be radiobiological advantages in terms of greater tumor or other target control efficacy for the same physical radiation dose.

30 Claims, 8 Drawing Sheets

(56) References Cited

U.S. PATENT DOCUMENTS

| | | |
|---|---|---|
| 6,537,052 B1 | 3/2003 | Adler |
| 6,559,610 B2 | 5/2003 | Tanaka |
| 6,714,620 B2 | 3/2004 | Caflisch et al. |
| 6,724,782 B2 | 4/2004 | Hartemann et al. |
| 6,977,987 B2 | 12/2005 | Yamashita et al. |
| 7,085,347 B2 | 8/2006 | Mihara et al. |
| 7,167,540 B2 | 1/2007 | Muller et al. |
| 7,180,243 B2 | 2/2007 | Secheresse et al. |
| 7,190,764 B2 | 3/2007 | Mori et al. |
| 7,206,379 B2 | 4/2007 | Lemaitre |
| 7,391,850 B2 | 6/2008 | Kaertner et al. |
| 7,486,775 B2 | 2/2009 | Forster et al. |
| 7,630,474 B2 | 12/2009 | Clayton |
| 7,741,624 B1 | 6/2010 | Sahadevan |
| 7,839,972 B2 | 11/2010 | Ruchala et al. |
| 8,027,431 B2 | 9/2011 | Stahl et al. |
| 8,039,819 B2 | 10/2011 | Faure et al. |
| 8,315,357 B2 | 11/2012 | Zhu et al. |
| 8,350,226 B2 | 1/2013 | Zdasiuk et al. |
| 8,405,044 B2 | 3/2013 | MacKinnon et al. |
| 2002/0191746 A1 | 12/2002 | Dinsmore |
| 2004/0082855 A1 | 4/2004 | Robar et al. |
| 2009/0212231 A1 | 8/2009 | Hill et al. |
| 2009/0252291 A1* | 10/2009 | Lu et al. ............ 378/65 |
| 2010/0228116 A1 | 9/2010 | Lu et al. |
| 2010/0246767 A1 | 9/2010 | Tanabe |
| 2011/0093243 A1 | 4/2011 | Tawhai et al. |
| 2012/0262333 A1 | 10/2012 | Trummer |
| 2012/0326636 A1 | 12/2012 | Eaton et al. |
| 2013/0016814 A1 | 1/2013 | Treas et al. |

OTHER PUBLICATIONS

DesRosiers, C., et al., "150-250 MeV electron beams in radiation therapy", Physics in Medicine and Biology, vol. 45, No. 7, 2000, pp. 1781-1805.

DesRosiers, Colleen M., "An evaluation of very high energy electron beams (up to 250 MeV) in radiation therapy", Dec. 2004, 163 pages.

Fuchs, Thomas, "Laser-accelerated particles: Investigations towards applications in radiotherapy", 2007, 152 pages.

Fuchs, T., et al., "Treatment planning for laser-accelerated very-high energy electrons." Physics in Medicine and Biology vol. 54, No. 11, 2009, pp. 3315-3328.

Glinec, Yannick, et al., "Radiotherapy with laser-plasma accelerators: Monte Carlo simulation of dose deposited by an experimental quasimonoenergetic electron beam", Medical Physics, vol. 33, No. 1, Jan. 2006, pp. 155-162.

Yeboah, C., et al., "Optimization of intensity-modulated very high energy (50-250 MeV) electron therapy", Physics in Medicine and Biology, vol. 47, No. 8, 2002, pp. 1285-1301, May 20, 2013.

Yeboah, C., et al., "Optimized treatment planning for prostate cancer comparing IMPT, VHEET and 15 MV IMXT", Physics in Medicine and Biology, vol. 47, No. 13, 2002, pp. 2247-2261.

International Search Report and Written Opinion of PCT Application No. PCT/US2013/025765, mailed Apr. 19, 2013, 20 pages.

\* cited by examiner

PLURIDIRECTIONAL VERY HIGH ELECTRON ENERGY RADIATION THERAPY SYSTEMS AND PROCESSES

CROSS-REFERENCES TO RELATED APPLICATIONS

The present application claims the benefit under 35 USC 119(e) of U.S. Provisional Application No. 61/606,408 filed Mar. 3, 2012; the full disclosure of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

The invention generally relates to radiation therapy and more particularly to systems and methods for very high electron energy radiation therapy.

BACKGROUND OF THE INVENTION

Major technical advances in radiation therapy in the past two decades have provided effective sculpting of 3-D dose distributions and spatially accurate dose delivery by imaging verification. These technologies, including intensity modulated radiation therapy (IMRT), hadron therapy, and image guided radiation therapy (IGRT) have translated clinically to decreased normal tissue toxicity for the same tumor control, and more recently, focused dose intensification to achieve high local control without increased toxicity, as in stereotactic ablative radiotherapy (SABR) and stereotactic body radiotherapy (SBRT).

One key remaining barrier to precise, accurate, highly conformal radiation therapy is patient, target and organ motion from many sources including musculoskeletal, breathing, cardiac, organ filling, peristalsis, etc. that occurs during treatment delivery, currently 15-90 minutes per fraction for state-of-the-art high-dose radiotherapy. As such, significant effort has been devoted to developing "motion management" strategies, e.g., complex immobilization, marker implantation, respiratory gating, and dynamic tumor tracking.

BRIEF SUMMARY OF THE INVENTION

A fundamentally different approach to managing motion is to deliver the treatment so rapidly that no significant physiologic motion occurs between verification imaging and completion of treatment. According to certain embodiments of the invention, an accelerator, more preferably a compact high-gradient, very high energy electron (VHEE) linear accelerator, which may be a standing wave linear accelerator, together with a delivery system capable of treating patients from multiple beam directions, potentially using all-electromagnetic or radiofrequency deflection steering is provided, that can deliver an entire dose or fraction of high-dose (e.g., 20-30 Gy) radiation therapy sufficiently fast to freeze physiologic motion, yet with a better degree of dose conformity or sculpting than conventional photon therapy. The term "sufficiently fast to freeze physiologic motion" in this document means preferably faster than one human breath hold, more preferably less than 10 seconds, even more preferably less than 5 seconds, even more preferably less than one heartbeat and most preferably less than a second. In addition to the unique physical advantages of extremely rapid radiation delivery, there may also be radiobiological advantages in terms of greater tumor control efficacy for the same physical radiation dose. Certain embodiments of the invention can also treat non-tumor targets, such as, by way of nonlimiting example, ablation or other treatment of: (1) nerves or facet joints for pain control; (2) foci in the brain for neuromodulation of neurologic conditions including pain, severe depression, and seizures; (3) portions of the lung with severe emphysema; and/or (4) abnormal conductive pathways in the heart to control refractory arrhythmias.

According to certain embodiments of the invention, there is provided a system for delivering very high electron energy beam to a target in a patient, comprising:

An accelerator capable of generating a very high electron energy beam;

A beam steering device capable of receiving the beam from the accelerator and steering the beam to the target from multiple directions; and A controller capable of controlling length of time that the beam irradiates the target, the length of time sufficiently fast to freeze physiologic motion, and to control the directions in which the beam steering device steers the beam to the target.

According to some embodiments, the controller is configured to receive information from an imaging device and use the information from the imaging device to control the directions in which the beam steering device steers the beam to the target.

According to some embodiments, the accelerator is a linear accelerator capable of generating a beam having energy of between 1 and 250 Mev, more preferably 50 and 250 MeV and most preferably between 75 and 100 MeV.

According to some embodiments, the time period is preferably faster than one human breath hold, more preferably less than 10 seconds, even more preferably less than 5 seconds, even more preferably less than one heartbeat and most preferably less than a second.

According to some embodiments, the beam steering device is an electro-magnetic device.

According to some embodiments, the beam steering device is a radiofrequency deflector device.

According to some embodiments, the beam steering device includes a gantry, the gantry including multiple beam ports.

According to some embodiments, the beam steering device includes a continuous annular gantry.

According to some embodiments, the beam steering device is capable of providing thin pencil beam raster scanning.

According to some embodiments, the beam steering system is capable of providing volume filling scanning.

According to some embodiments, the beam steering device includes no mechanical moving parts.

According to other embodiments, there is provided a system for delivering very high electron energy beam to a target in a patient, comprising:

An accelerator capable of generating a very high electron energy beam;

A beam steering device capable of receiving the beam from the accelerator and steering the beam to the target from multiple directions;

A controller capable of controlling length of time that the beam irradiates the target, the length of time sufficiently fast to freeze physiologic motion, and to control the directions in which the beam steering device steers the beam to the target; and An imaging device capable of generating images of the target and providing information from the imaging device to the controller to control the directions in which the beam steering device steers the beam to the target.

According to some embodiments, the imaging device is capable of providing information to the controller to trigger when the system delivers the beam to the target.

According to some embodiments, using information from the imaging device, the system is capable of automatically delivering the beam to the target from multiple predetermined directions at multiple predetermined points in time.

According to some embodiments, the accelerator is a linear accelerator capable of generating a beam having energy of between 1 and 250 Mev, more preferably 50 and 250 MeV and most preferably between 75 and 100 MeV.

According to some embodiments, the time period is preferably faster than one human breath hold, more preferably less than 10 seconds, even more preferably less than 5 seconds, even more preferably less than one heartbeat and most preferably less than a second.

According to some embodiments, the beam steering device is an electro-magnetic device.

According to some embodiments, the beam steering device is a radiofrequency deflector device.

According to some embodiments, the beam steering device includes no mechanical moving parts.

According to other embodiments, there is provided a method for delivering a beam of very high electron energy to a target in a patient, comprising:

Providing a system for delivering very high electron energy beam to a target in a patient, the system comprising:
An accelerator capable of generating a very high electron energy beam;
A beam steering device capable of receiving the beam from the accelerator and steering the beam to the target from multiple directions; and
A controller capable of controlling length of time that the beam irradiates the target, the length of time sufficiently fast to freeze physiologic motion, and to control the directions in which the beam steering device steers the beam to the target; and
Actuating the system to cause it to deliver the beam to the target.

According to some embodiments, providing the system includes providing an accelerator that is capable of generating a beam having energy of between 1 and 250 Mev, more preferably 50 and 250 MeV and most preferably between 75 and 100 MeV.

According to some embodiments, providing the system includes providing a controller capable of controlling length of time that the beam irradiates the target, the time period preferably faster than one human breath hold, more preferably less than 10 seconds, even more preferably less than 5 seconds, even more preferably less than one heartbeat and most preferably less than a second.

According to some embodiments, providing the system includes providing a beam steering device that is an electromagnetic device.

According to some embodiments, providing the system includes providing a beam steering device that is a radiofrequency deflector device.

According to some embodiments, providing the system includes providing a beam steering device that includes no mechanical moving parts.

According to some embodiments, there is further provided a controller that is configured to receive information from an imaging device and use the information from the imaging device to control the directions in which the beam steering device steers the beam to the target.

According to some embodiments, there is further provided an imaging device capable of generating images of the target and providing information from the imaging device to the controller to control the directions in which the beam steering device steers the beam to the target.

According to some embodiments, providing the imaging device includes providing an imaging device that is capable of providing information to the controller to trigger when the system delivers the beam to the target.

According to some embodiments, providing the imaging device includes providing an imaging device wherein, using information from the imaging device, the system is capable of automatically delivering the beam to the target from multiple predetermined directions at multiple predetermined points in time.

According to other embodiments, there is also provided a system for delivering a transverse-modulated electron beam to a target in a patient, comprising:
A photoelectron gun configured to generate a transverse-modulated electron beam from an optical image produced by a light source such as a laser and projected on a photocathode;
An accelerator capable of increasing the energy level of the transverse-modulated electron beam to a predetermined level;
A beam steering device capable of receiving the transverse-modulated electron beam from the accelerator and steering the transverse-modulated electron beam to the target from multiple directions; and
A controller capable of controlling length of time that the transverse-modulated electron beam irradiates the target, the length of time sufficiently fast to freeze physiologic motion, and to control the directions in which the beam steering device steers the transverse-modulated electron beam to the target.

DETAILED DESCRIPTION OF THE INVENTION

A. Significance

In the U.S., cancer has surpassed heart disease as the leading cause of death in adults under age 85, and of the 1.5 million patients diagnosed with cancer each year, about two thirds will benefit from radiation therapy (RT) at some point in their treatment, with nearly three quarters of those receiving RT with curative intent. Worldwide, the global burden of cancer is increasing dramatically owing to the aging demographic, with an incidence of nearly 13 million per year and a projected 60% increase over the next 20 years, and the number of patients who could benefit from RT far exceeds its availability. Moreover, even when RT is administered with curative intent, tumor recurrence within the local radiation field is a major component of treatment failure for many common cancers. Thus, improvements in the efficacy of and access to RT have tremendous potential to save innumerable lives.

Although there have been major technological advances in radiation therapy in recent years, a fundamental remaining barrier to precise, accurate, highly conformal radiation therapy is patient, target, and organ motion from many sources including musculoskeletal, breathing, cardiac, organ filling, peristalsis, etc. that occurs during treatment delivery. Conventional radiation delivery times are long relative to the time scale for physiologic motion, and in fact, more sophisticated techniques tend to prolong the delivery time, currently 15-90 minutes per fraction for state-of-the-art high-dose radiotherapy. The very fastest available photon technique (arc delivery with flattening filter free mode) requires a minimum of 2-5 min to deliver 25 Gy. Significant motion can occur during these times.

Even for organs unaffected by respiratory motion, e.g., the prostate, the magnitude of intrafraction motion increases significantly with treatment duration, with 10% and 30% of treatments having prostate displacements of >5 mm and >3 mm, respectively, by only 10 minutes elapsed time. As such, considerable effort has been devoted to developing "motion management" strategies in order to suppress, control, or compensate for motion. These include complex immobilization, fiducial marker implantation, respiratory gating, and dynamic tumor tracking, and in all cases still require expansion of the target volume to avoid missing or undertreating the tumor owing to residual motion, at the cost of increased normal tissue irradiation.

Several factors contribute to long delivery times in existing photon therapy systems. First, production of x-rays by Bremsstrahlung is inefficient, with less than 1% of the energy of the original electron beam being converted to useful radiation. Second, collimation, and particularly intensity modulation by collimation, is similarly inefficient as the large majority of the beam energy is blocked by collimation. Third, using multiple beam angles or arcs to achieve conformal dose distributions requires mechanical gantry motion, which is slow. Treatment using protons or other heavier ions has dosimetric advantages over photon therapy, and these particles can be electromagnetically scanned very rapidly across a given treatment field. However changing beam directions still requires mechanical rotation of the massive gantry, which is much larger and slower than for photon systems. The cost and size of these systems also greatly limits their accessibility.

Very high-energy electrons (VHEE) in the energy range of 50-250 MeV have shown favorable dose deposition properties intermediate between megavoltage (MV) photons and high-energy protons. Without the need for inefficient Bremsstrahlung conversion or physical collimation, and with a smaller steering radius than heavier charged particles, treatment can be multiple orders of magnitude faster than any existing technology in a form factor comparable to conventional medical linacs. According to certain embodiments of the invention, a compact high-gradient VHEE accelerator and delivery system is provided that is capable of treating patients from multiple beam directions with great speed, using electro-magnetic, radiofrequency deflection or other beam steering devices. Such embodiments may deliver an entire dose or fraction of high-dose radiation therapy sufficiently fast to freeze physiologic motion, yet with a better degree of dose conformity or sculpting, and decreased integral dose and consequently decreased risk of late toxicities and secondary malignancies, than the best MV photon therapy. Suitable energy ranges in accordance with certain embodiments of the invention are 1-250 MeV, more preferably 50-250 MeV, and most preferably 75-100 MeV. Again, as described in the Summary section above, the term "sufficiently fast to freeze physiologic motion" in this document means preferably faster than one human breath hold, more preferably less than 10 seconds, even more preferably less than 5 seconds, even more preferably less than one heartbeat and most preferably less than a second.

Figure 1:
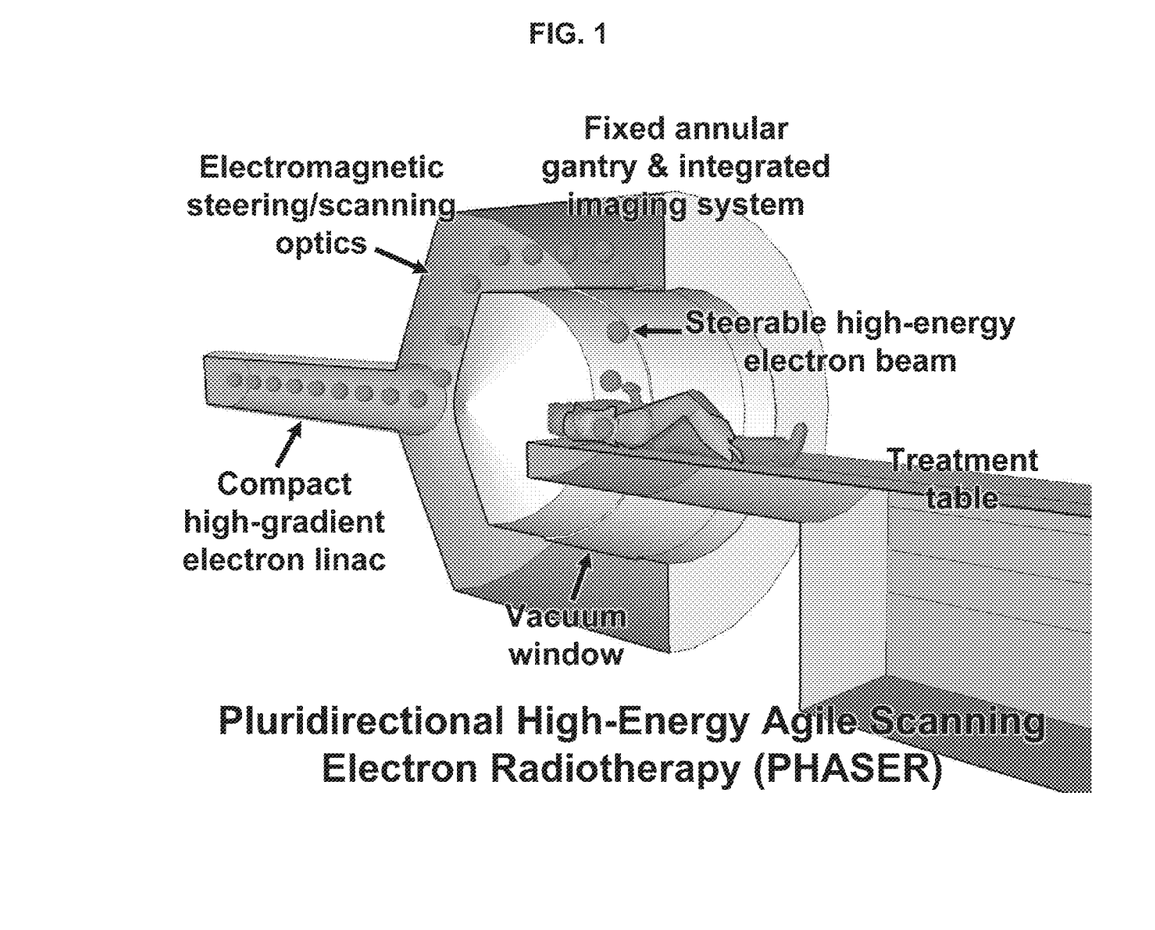
FIG. 1 is a schematic representation of one embodiment of the invention, showing beam access from a large number of axial directions by electromagnetic- or radiofrequency deflection steering.

According to some embodiments, a major technological advance is extremely rapid or near instantaneous delivery of high dose radiotherapy that can eliminate the impact of target motion during RT, affording improved accuracy and dose conformity and potentially radiobiological effectiveness that will lead to improved clinical outcomes. Rapid imaging and treatment can also lead to greater clinical efficiency and patient throughput. For standard treatments, the room occupancy time can be reduced to less than 5 minutes. There can also be a great practical advantage for special populations like pediatric patients who normally require general anesthesia for adequate immobilization during long treatments, and who can instead be treated with only moderate sedation for such rapid treatments. Such advantages can be achieved, according to some embodiments, in a compact physical form factor and low cost comparable to conventional photon therapy systems, and much lower than hadron therapy systems. One embodiment is shown in FIG. 1, which shows a system wherein beam access from a large number of axial directions is achieved by electromagnetic steering without moving parts or with a minimum of moving parts, for extremely fast highly conformal radiotherapy. The system shown in FIG. 1 includes a compact linear accelerator, a beam steering device, and a controller for controlling the very high electron energy beam that is delivered to the patient. The embodiment can also include an integrated imaging device that obtains images of portions of the patient including the tumor or other site to be treated. The imaging device can also provide information to allow for control of the beam steering device in order to control directions from which the beam is delivered, and timing of the beam, among other variables.

Furthermore, the prolonged treatment times of conventional highly conformal RT are sufficiently long for repair of sublethal chromosomal damage to occur during treatment, potentially reducing the tumoricidal effect of the radiation dose. Thus in addition to the unique physical advantages of extremely rapid radiation delivery, there may also be dose advantages. It is hypothesized that the treatment times sufficiently fast to freeze physiologic motion that are made possible by certain embodiments of the invention may be more biologically effective, producing enhanced tumor cell killing for the same physical dose. Differences between certain embodiments of the invention and conventional photon therapy that impact biological effectiveness include a much faster delivery time and differences in the radiation quality.

Dose rate effects are well described in the radiobiology literature, in which prolongation of delivery times results in decreased cell killing. The main mechanism known to be responsible for this effect is repair of potentially lethal DNA double strand breaks (DSB) during the interval over which a given dose of radiation is delivered. Several in vitro studies have demonstrated significantly decreased cell killing when delivery is protracted from a few minutes to tens of minutes. However, there is a lack of consensus in the literature regarding the kinetics of sublethal damage (SLD) repair, with some studies suggesting that components of SLD repair may have repair half-times of as little as a few minutes. If so, shortening the delivery times even from a few minutes to a time period sufficiently fast to freeze physiologic motion has the potential to increase tumor cell killing.

B. Beam Steering

Some embodiments of the invention take advantage of the fact that electrons are relatively easier to manipulate using electric and magnetic fields. Charged particles such as electrons and protons can be produced as spatially coherent beams that can be steered electromagnetically or with radiofrequency deflection with high rapidity. Thus, direct treatment with scanned charged particle beams can eliminate the inefficiencies of Bremsstrahlung photon multiple beams from different directions toward the target in the patient. All conventional radiation therapy systems accomplish multidirectional treatment by mechanically rotating a gantry, or an entire compact linac, or even cyclotron, directing radiation to the target from one direction at a time.

As a preliminary matter, at the end of the accelerator structure the beam must be deflected and then transported to the exit port and toward a target in or on the patient, such as a tumor in the patient. At the exit port the beam must be steered again to change the exit angle and/or beam size to adapt to the treatment plan. Electro-magnetic and/or RF deflector steering systems will manipulate the electron beam.

A variety of gantry designs are potentially available, from simple to complex, ranging from multiple discrete beam ports arranged around the patient to a continuous annular gantry to allow arbitrary incident axial beam angles. The design depends on a number of factors, including scanning strategies such as thin pencil beam raster scanning vs. volume filling with non-isocentric variable-size shots, or use of transverse modulation of the electron beam profile.

According to one embodiment, the steering system of the electron beam starts at the end of the accelerator structure with a two-dimensional deflector, which guides the beam into one of multiple channels. Once the beam enters a specific channel it is guided all the way to the exit of the channel, which is perpendicular to the axis of the patient. The guidance through the channels is achieved using low aberration electron optics. At the exit of each channel another small 2-D deflector can be added to scan the beam over a target. The number of channels can then be about 10-50. For a given channel width, a larger initial deflection would increase the number of channel entry ports that fit into the circumference swept by the beam. Thus if the field strength were increased, the number of channels could be increased to 100 or more.

Because a linear accelerator will typically consume 50 to 100 MW of peak power to achieve 100 MeV of acceleration, over a length of 2 to 1 m respectively, potential RF deflectors can be considered. These have the advantage of being ultra-fast and permit capitalization on the RF infrastructure that is used for the main accelerator structure. In any event, the delivery system is preferably optimized to achieve high-dose treatment times sufficiently fast to freeze physiologic motion.

Beam steering systems according to certain embodiments of the invention adopt a design that uses a smaller number of discrete beam channels, for example 3-10, that are mechanically rotated with the gantry around the patient. The initial deflector at the exit of the accelerator rapidly steers beams into the channels as they rotate. Although the ideal is to eliminate the need for any mechanical moving parts, some advantages of this design include: arbitrary rotational angular resolution despite a fixed number of beam channels; reduced complexity and possibly cost given the smaller number of beam channels needed to achieve equivalent angular coverage; and the larger space between beam channels which makes it more straightforward to incorporate an x-ray source and detecting array for imaging, which when rotated provides integrated computed tomography imaging. The rate of mechanical rotation preferably provides full angular coverage sufficiently fast to freeze physiologic motion. The greater the number of beam channels, the less rotational speed required to meet this condition as a general matter.

One innovation of certain embodiments of the invention is to eliminate mechanical gantry rotation, thus a beam steering system with no mechanical moving parts. One such embodiment is illustrated in FIG. 1, in which there is a gantry through which a charged particle beam is electromagnetically steered or steered using radiofrequency deflection to the target from any axial direction and a limited range of non-coplanar directions in addition. An alternative implementation is to use multiple discrete beam ports arranged radially around the patient, with the beam being steered through each of the ports to the target for multidirectional beam arrangements. Another alternative implementation is to have multiple accelerating structures, one for each of a set of beam ports arranged radially around the patient.

Such novel treatment system geometries and steering systems can greatly enhance the treatment delivery speed of radiation therapy using any type of charged particle. Combining it with high-energy electrons in the 1-250 MeV range, more preferably the 50-250 MeV range, most preferably the 75-100 MeV range, has the following additional advantages: (1) Conformal dose distributions to both superficial and deep targets in patients superior to what can be achieved with conventional high-energy photon therapy; (2) Compactness of the source and power supply, which by using high-gradient accelerator designs such as those based wholly or partially on accelerators developed or in development at the SLAC National Accelerator Laboratory (SLAC) as described in Section C.iii below can accelerate electrons up to these energies in less than 2 meters; (3) Compactness of the gantry/beam ports compared to protons or ions because of the smaller electro-magnetic fields needed for electrons. This results in a system of comparable cost and physical size to existing conventional photon radiotherapy treatment systems, yet with better dose distributions and far faster dose delivery.

If treatment with photon beams is still desired, an alternative embodiment is to incorporate in this geometry an array of high density targets and collimator grid in place of a single target/multi-leaf collimator combination, one per beam port in the case of discrete beam ports, or mounted on a rapidly rotating closed ring and targeted by the scanned electron beam in the case of an annular beam port, in order to produce rapidly scanned, multidirectional photon beams. While this approach may be subject to the inefficiency of Bremsstrahlung conversion, the speed limitations of conventional mechanical gantry and multi-leaf collimator motions may be essentially eliminated. The main potential advantage of this implementation is that existing commercial electron linacs in a lower energy range could be used as the source.

In addition to extremely rapid dose delivery, certain embodiments of the invention naturally facilitate rapid image-guidance to ensure accuracy. By adjusting the energy of the scanned electron beam and directing it to an annular target or a fixed array of targets, with an appropriately arranged detector array, extremely fast x-ray computed tomography (CT) or digital tomosynthesis images can be obtained and compared to pre-treatment planning images immediately before delivery of the dose. Alternative embodiments can include integration of more conventional x-ray imaging or other imaging modalities, positron emission tomography and other options described in Section D.3 below.

C. Monte Carlo Simulation Design Considerations

One approach in designing certain embodiments of the invention is to proceed using some or all of the following: (1) Monte Carlo simulations to determine optimal operating parameters; (2) experimental measurements of VHEE beams to validate and calibrate the Monte Carlo codes; (3) implementation factors for practical, cost-efficient and compact designs for the systems; and (4) experimental characterization of key radiobiological aspects and effects.

1. Monte Carlo (MC) Simulation

MC simulations of VHEE of various energies have been performed on a sample case to estimate the range of electron energies needed to produce a plan comparable to optimized photon therapy. Dose distributions were calculated for a simulated lung tumor calculated on the CT data set of an anthropomorphic phantom.

Specifically, an optimized 6 MV photon beam Volumetric Modulated Arc Therapy Stereotactic Ablative Body Radiotherapy (VMAT SABR) plan calculated in the Eclipse treatment planning system, and simplistic conformal electron arc plans with 360 beams using a commonly available 20 MeV energy and a very high 100 MeV energy calculated with the EGSnrc MC code [Walters B, Kawrakow I, and Rogers DWO, DOSXYZnrc, Users Manual, 2011, Ionizing Radiation Standards National Council of Canada. p. 1-109. (http://irs.inms.nrc.ca/software/beamnrc/documentation/pirs794/), incorporated herein by this reference], were compared.

Figure 2:
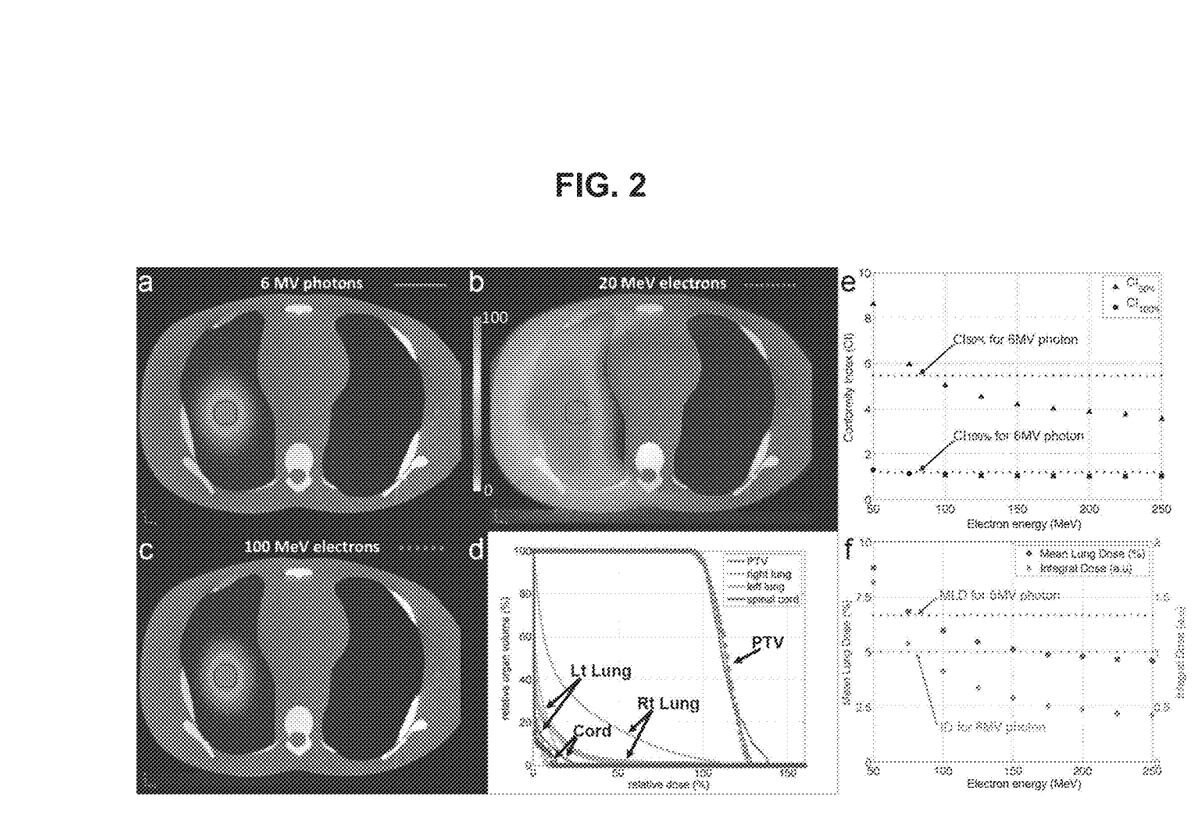
FIG. 2 shows comparative simulation results of SABR for an early stage lung tumor using 6 MV photons, 20 MeV electrons, and 100 MeV electrons.

FIG. 2 shows axial images of simulation of SABR for an early stage lung tumor: dose distribution in an anthropomorphic phantom for a state-of-the-art 6 MV photon VMAT plan (FIG. 2a), a conformal electron arc plan using currently available 20 MeV electron beam (FIG. 2b), and a conformal electron arc plan using a 100 MeV electron beam as might be delivered by an embodiment of the invention (FIG. 2c). A graphical representation shows dose volume histogram ("DVH") of the planning target volume ("PTV") (delineated in black in the axial images) and critical organs: DVHs for 6 MV photons are shown in solid, 20 MeV electrons in dotted, and 100 MeV electrons in crossed lines (FIG. 2d). The plans were normalized to produce the same volumetric coverage of the PTV by the prescription dose. While conventional 20 MeV electrons results in poor conformity, the 100 MeV electron plan, even without optimization, is slightly more conformal than the 6 MV photon VMAT plan. Simulating conformal electron arcs across an energy range of 50-250 MeV (FIGS. 2e, 2f) demonstrates that both the high (100%) and intermediate (50%) dose conformity indices (CI100% and CI50%) as well as the mean lung dose and total body integral dose are superior for electron energies of ~80 MeV and higher for this selected clinical scenario. With inverse optimization, superior plans with even lower electron energies should be possible.

As shown in FIG. 2, the axial views of the dose distributions demonstrate that when all the plans are normalized to produce the same volumetric coverage of the target, the dose conformity of the 20 MeV beam is poor whereas the 100 MeV electron beam, even without inverse optimization, generates a dose distribution equivalent to the state-of-the-art 6 MV photon beam VMAT plan. In fact, the DVH's of the target and critical structures for the three beams demonstrate slightly better sparing of critical structures with the 100 MeV electron plan compared to the 6 MV photon plan. As shown in FIGS. 2e and 2f, at electron energies above ~80 MeV, simple conformal electron arc plans (normalized to produce the same volumetric coverage of the target) are superior to the optimized 6 MV photon VMAT plan in terms of conformity, with conformity index defined as the ratio of the given percent isodose volume to the PTV, and the normal organ doses (mean lung dose) and total body integral dose (expressed in arbitrary units normalized to the photon plan). In preliminary simulations of this selected clinical scenario, the inventors have found electron energies of 75-100 MeV to produce plans of comparably high to superior quality compared to the best photon plans, and anticipate that plan optimization will produce superior plans with even lower electron energies. For example, the inventors have used Monte Carlo simulations to demonstrate that an 8 cc lung tumor could be treated with 100 MeV electrons to a dose of 10 Gy in 1.3 seconds.

Further optimization of the electron plan can help to define the minimum electron beam energy with a comparable dose distribution to the best photon VMAT plan. In preliminary simulations of this selected clinical scenario, the inventors have found electron energies of 75-100 MeV to produce plans of comparably high quality to the best photon plans, and anticipate superior plans with plan optimization.

2. Experimental Measurement of VHEE Beams a. Monte Carlo Simulations

Figure 3:
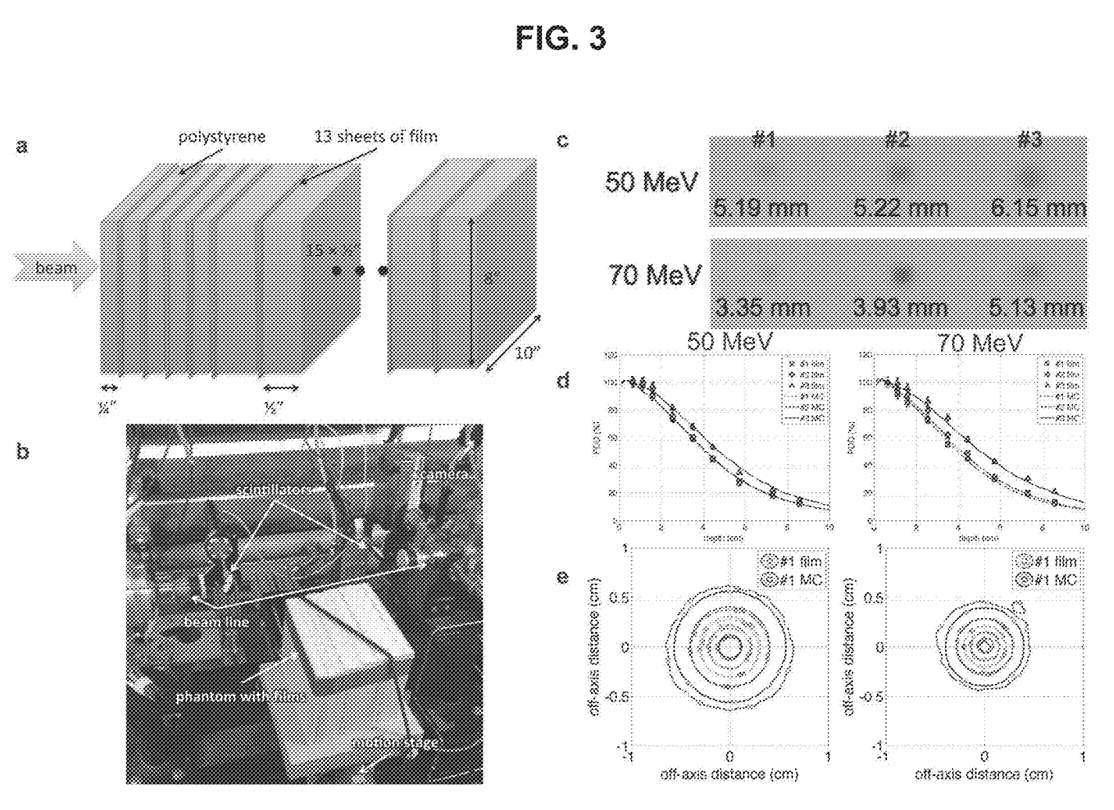
FIG. 3 is a schematic (a) and photograph (b) of the experimental setup for film measurements (c) of very high energy electron beams at the Next Linear Collider Test Accelerator (NLCTA) beam line at the SLAC National Accelerator Laboratory (SLAC), together with Monte Carlo simulations (solid lines) and film measurements (markers) of percentage depth dose curves (d) and beam profiles taken at 6 mm depth (e) for 50 MeV and 70 MeV beams, respectively.

To demonstrate the accuracy of Monte Carlo calculations with VHEE beams, the inventors experimentally measured the dose distribution and depth dose profiles at the NLCTA facility at SLAC. Of note, the NLCTA employs compact high-gradient linear accelerator structures which can produce beams that are relevant to those potentially suitable for certain embodiments of the invention. The inventors assembled a dosimetry phantom by sandwiching GAFCHROMIC EBT2 films (International Specialty Products, Wayne, N.J.) between slabs of tissue equivalent polystyrene as shown in FIG. 3. FIG. 3a is a schematic and FIG. 3b is a photograph of the experimental setup for film measurements (FIG. 3c) of very high-energy electron beams at the NLCTA beam line at SLAC. Monte Carlo simulations and film measurements of percentage depth dose curves (FIG. 3d) and 2-D dose distributions taken at 6 mm depth (FIG. 3e) for 50 MeV and 70 MeV beams demonstrate a high degree of agreement between calculation and measurement.

By way of procedure and in greater detail, the phantom as shown in FIG. 3a was irradiated with 50 MeV and 70 MeV beams. Three beam sizes ranging from 3.35 to 6.15 mm were tested for each energy level. The energy was measured by a spectrometer upstream from the location of the experiment and the beam size was measured by two scintillating screens using two cameras just before and after the phantom with the phantom removed from the beam line (FIG. 3b). The films were calibrated with a clinical electron beam at 12 MeV. MC simulations have demonstrated no energy dependence of the film response at electron energies above 1 MeV. The number of particles required to irradiate the films to dose levels between 1-5 Gy to match the dynamic range of the film was determined for each beam size using MC simulations and used in the experiment. The charge was set to 30 pC/pulse corresponding to $1.9 \times 10^8$ electrons and the pulse rate was reduced to 1 Hz for easier control of the exposure. The number of pulses varied from 2 to 40 pulses depending on the beam size. The experimental and calibration films were read out in a flatbed scanner (Epson Perfection V500, Long Beach, Calif.) with 0.1 mm pixels 24 hours after irradiation (FIG. 3c) and central axis percentage depth dose (PDD) curves and 2-dimensional dose distributions at various depths were plotted. The experimental setup was simulated in the MCNPX 5.0 MC code [Palowitz D B, MCNPX User's Manual, Version 2.7.0, 2011 (http://mcnpx.lanl.gov/documents.html) incorporated herein by this reference].

The simulations are compared to measurements in FIG. 3d-e. Good agreement was observed for both the PDD curves and beam profiles for 50 and 70 MeV. These preliminary results indicate that dose from VHEE beams can be measured with GAFCHROMIC films and that VHEE beams can be accurately simulated with the GEANT4 code.

In the arrangement shown in FIG. 3b, a 50-μm vacuum window made of stainless steel was used to interface the accelerator line with open air, in which the dose phantom (FIG. 2a) was placed. The stainless window was found to cause significant angular beam spreading, so that the simulations were also performed with a beryllium window which imparted less beam spreading. While a vacuum window is necessary to separate the vacuum of the accelerator beam line from the open air and the patient, significant angular spread will adversely affect beam performance and clinical accuracy. The angular spread from a thinner beryllium window was still present but it was much smaller than steel, due to beryllium's low atomic number.

b. Cross Validation of Monte Carlo Codes

Figure 4:
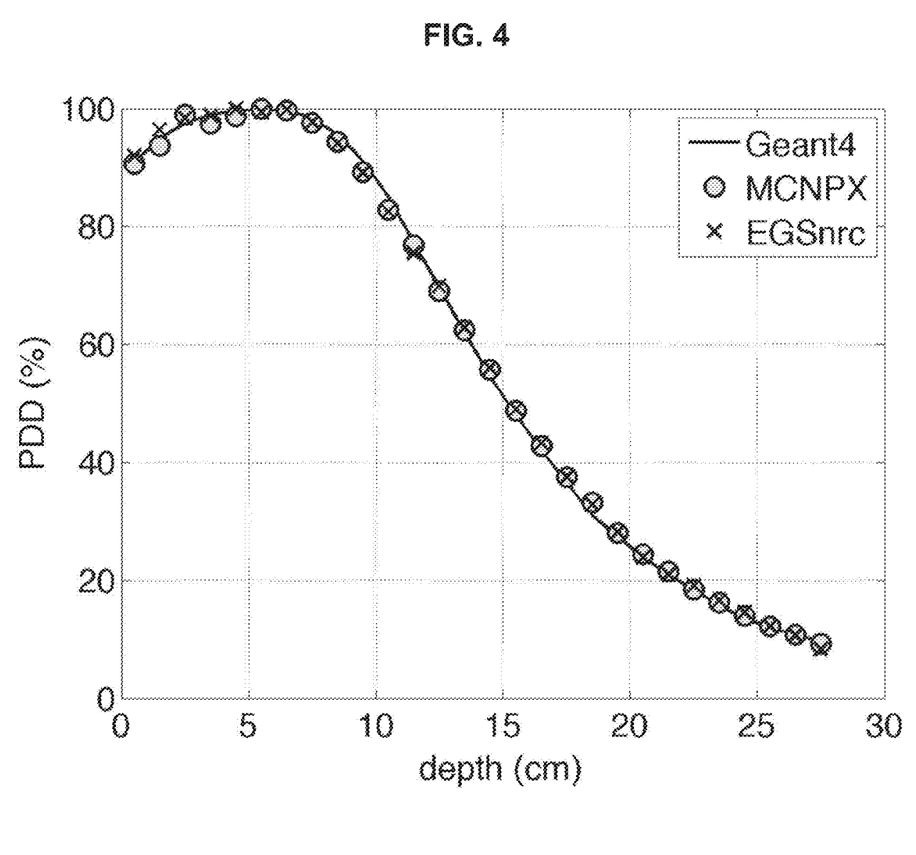
FIG. 4 shows graphic representations of percentage depth doses for a 2×2 cm 100 MeV electron beam in a water phantom, simulated using three independent Monte Carlo codes.
Figure 7:
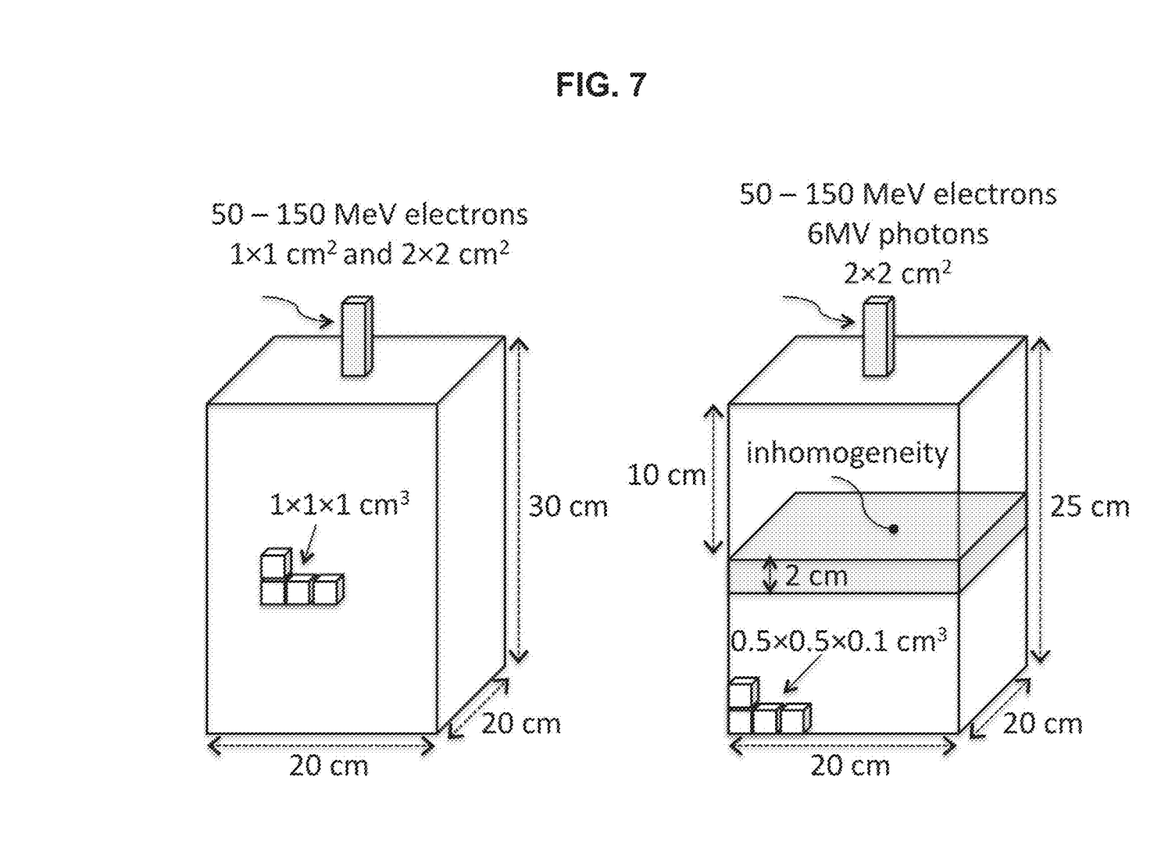
FIG. 7 shows water phantoms used in Monte Carlo simulations conducted in accordance with certain embodiments of the invention.

The inventors performed Monte Carlo simulations using three independent codes for identical geometries to determine the consistency of calculated doses. The dose deposition of a number of rectangular electron beams incident on a 20×20× 30 cm water phantom (as shown in FIG. 7a) was simulated in the GEANT4, MCNPX, and EGSnrc MC codes. The simulated electron beam energies were 50, 75, 100, and 150 MeV with beam sizes of 1×1 cm and 2×2 cm. The central-axis PDDs were plotted and compared for all three MC codes. Excellent agreement was found between the codes for all of these comparisons, as shown in FIG. 4, which shows PDD for a 2×2 cm 100 MeV electron beam, simulated using the three Monte Carlo codes.

c. VHEE Tissue Interactions

Figure 5:
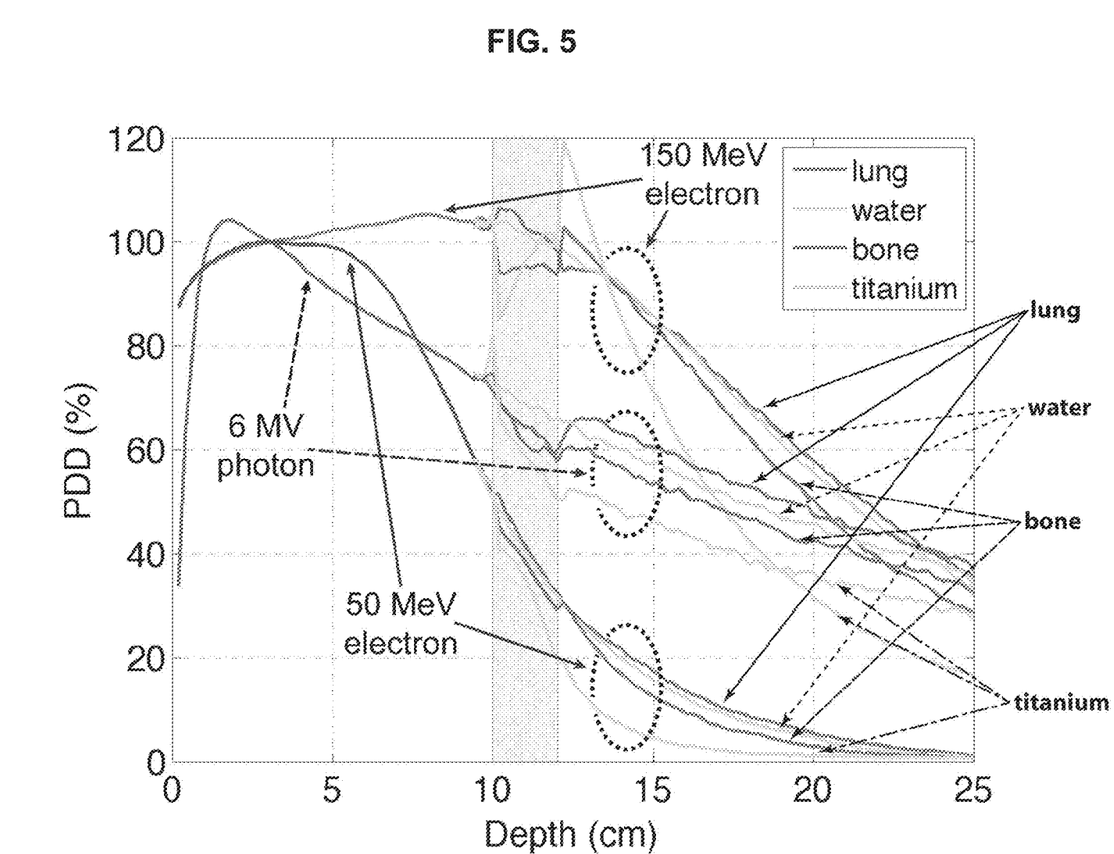
FIG. 5 shows graphic representations of percentage depth doses for 2×2 cm 50 and 150 MeV electron beams compared to 6 MV photons in a water phantom, with 2 cm thick heterogeneous tissue at 10 cm depth.

Monte Carlo simulations were performed to evaluate the impact of various tissue heterogeneities on VHEE beams relative to MV photon beams. FIG. 5 shows PDD curves for 2×2 cm 50 and 150 MeV electron beams compared to 6 MV photons in a water phantom with 2 cm thick heterogeneous tissue at 10 cm depth, normalized to identical dose at 3 cm depth. As shown in FIG. 5, the 50 and 150 MeV VHEE beams are less sensitive to tissue heterogeneity over the density range from lung tissue to titanium prosthetic implants compared to 6 MV photons.

Figure 6:
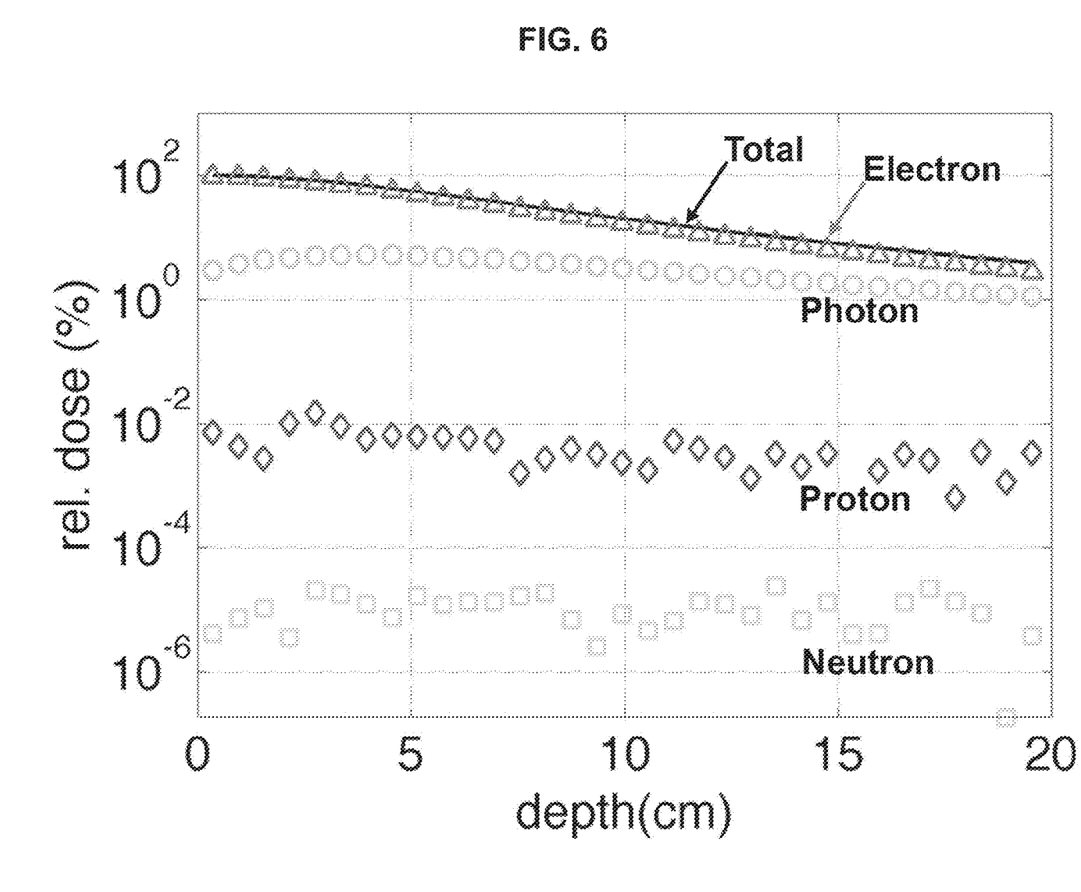
FIG. 6 shows graphic representations of relative contribution to dose from a 100 MeV electron beam vs. secondary generated particles (logarithmic scale).

Contribution of secondary particles produced by Bremsstrahlung and electronuclear interactions to the dose from VHEE beams were also analyzed. FIG. 6 shows relative contribution to dose from a 100 MeV electron beam vs. secondary generated particles (log scale). As shown in FIG. 6, for a 100 MeV electron beam, nearly all the deposited dose is due to electrons, with a minor contribution from Bremsstrahlung x-rays, and far lower dose from protons and neutrons. FIG. 6 also shows that dose from neutrons is far less than with 15-18 MV photons or high-energy protons. This holds for 50 and 70 MeV electrons as well (not shown). For a 25 Gy SABR treatment of a 2 cm diameter target, an upper limit of total body neutron dose is estimated to be 0.6 mSv based on MC simulations. This is in contrast to more than 1-2 orders of magnitude greater estimated neutron doses of 9-170 mSv for scanning beam proton therapy and 15-18 MV photon IMRT for the same clinical scenario, based on published measurements of ambient neutron doses [Schneider U, Agosteo S, Pedroni E, and Besserer J., "*Secondary neutron dose during proton therapy using spot scanning*," International Journal of Radiation Oncology Biology Physics, 2002; 53(1): 244-251. (PMID: 12007965); Howell R M, Ferenci M S, Hertel N E, Fullerton G D, Fox T, and Davis L W, "*Measurements of secondary neutron dose from* 15 *MV and* 18 *MV IMRT*," Radiation Protection Dosimetry, 2005; 115(1-4): 508-512. (PMID: 16381776) both of which are incorporated herein by this reference]. An advantage of such potential designs according to certain embodiments compared to >8 MV photon and scanning beam or passive scattering proton therapies is elimination of need for beam modifying structures prior to beam incidence on the patient, in which most neutrons are generated with existing modalities.

d. Tissue Inhomogeneities

The effect of tissue inhomogeneities on dose deposition of VHEE beams has been studied by the inventors. A 20×20×25 cm3 water phantom with 0.5×0.5×0.1 cm3 voxels and a 2-cm thick inhomogeneity placed at 10 cm depth was built (FIG. 7b). The 2-cm thick slab was consequently filled with lung with mass density p of 0.368 g/cm3, adipose (p=0.950 g/cm3), ribs (p=1.410 g/cm3), and cortical bone (p=1.920 g/cm3) tissue to assess the effect of human tissue inhomogeneities. The tissue composition was obtained from the ICRU-44 document [ICRU. Tissue substitutes in radiation dosimetry and measurement, 1989 (incorporated herein by this reference)]. Moreover, the effect of metals, such as hip prostheses, dental fillings, and surgical clips, was investigated by simulating a steel slab (ρ=8.030 g/cm3). Doses deposited by 50, 100, and 150 MeV electron beams, as well as 6 MV photon beam interacting with the inhomegeneity slab were simulated. The DOSXYZnrc code was chosen for this task due to its simplicity of use and its shortest calculation times. The statistical uncertainties in all central axis voxels were below 1%.

3. Ultra-High Gradient Accelerator Structure Design

Pluridirectional very high electron energy radiation therapy systems and processes according to various embodiments of the invention can be created with various types of electron source. There are a number of potential sources of very high-energy electrons in the range of, for example, up to about 250 MeV. A non-exhaustive list includes cyclotrons, synchrotrons, linacs (which can include more conventional designs with greater length), racetrack microtrons, dielectric wall accelerators, and laser plasma wakefield accelerator sources. Some of these are large and would need to be housed in a separate room. Some are not very mature technologies. In terms of goals of certain embodiments of the invention which can include any or all of compactness (entire system fitting within existing medical linac vaults without a separate room), power requirements, cost, repetition rates, compatibility with intensity modulation techniques described in this document, and other practical considerations, compact very high-gradient standing wave linear accelerators such as those developed at SLAC as described in the two paragraphs immediately below, or derivatives of them, may be at least a logical starting point, although other currently existing or future options should not be ruled out.

Highly efficient π-mode standing wave accelerator structures have been developed at SLAC for the project formerly known as the Next Linear Collider, a positron-electron collider at 500 GeV energy for high-energy physics research [Dolgashev V, Tantawi S, Higashi Y, and Spataro B, "*Geometric dependence of radio-frequency breakdown in normal conducting accelerating structures*," Applied Physics Letters, 2010; 97(17). (http://apl.aip.org/resource/1/applab/v97/i17/p171501_s1) incorporated herein by this reference (hereinafter sometimes "Dolgashev 2010"]. Such accelerators are capable of accelerating electrons to 100 MeV within 1 meter [Id.] using an optimized accelerating waveguide powered by a 50 MW 11.4 GHz microwave generator (klystron) [Caryotakis G. Development of X-band klystron technology at SLAC. Proceedings of the 1997 Particle Accelerator Conference, 1997; 3: 2894-2898. (http://ieeexplore.ieee.org/xpls/abs_all.jsp?arnumber=752852) incorporated herein by this reference]. In order to produce a practical system in terms of cost and size, optimized designs according to certain embodiments of the invention allow both economical production and high performance to minimize the treatment time while allowing maximum possible flexibility in beamlet shapes, directionality, and energy.

Furthermore, it has been shown that coupling a series of small sections of standing-wave accelerators with a distributed radiofrequency (RF) network makes it possible to design a system without any reflection to the RF source [Tantawi S G, "*rf distribution system for a set of standing-wave accelerator structures*," Physical Review Special Topics-Accelerators and Beams, 2006; 9(11) (http://prst-ab.aps.org/abstract/PRSTAB/v9/i11/e112001) incorporated herein by this reference (hereinafter, "Tantawi 2006"]. Building on these developments, a practical implementation of a standing-wave accelerator structure has been designed [Neilson J, Tantawi S, and Dolgashev V, "Design of RF feed system and cavities for standing-wave accelerator structure," Nuclear Instruments and Methods in Physics Research A: Accelerators, Spectrometers, Detectors and Associated Equipment, 2011; 657(1): 52-54. (http://www.sciencedirect.com/science/article/pii/S0168900211008898) incorporated herein by this reference (hereinafter, "Neilson 2011"] that is designed to accelerate electrons to 100 MeV within one meter. Such accelerators can serve as a basis for or be relevant to certain embodiments of the invention.

D. Other Design Issues

1. Design Options for the Injector System

To inject the required low charge bunch into accelerators according to certain embodiments of the invention, several possibilities are available. Those include a photo-injector RF gun. Additional options can be considered to reduce the cost and size of the system, including a variety of field emitter configurations and RF thermionic guns.

2. Optimization of the RF Source by the Addition of a Pulse Compression System

RF source requirements depend ultimately, at least in part, on the accelerator design. With the optimized cavities as described above, it is projected that a 50 MW source at X-band will be sufficient for a 2 meter accelerator operating at 50 MV/m. This type of source is available at SLAC and is being commercialized by Communications & Power Industries (Palo Alto, Calif.). With the use of a pulse compression system it may be possible to either reduce the cost and sophistication of the RF source dramatically or make the accelerator structure more compact by reducing the length to 1 meter. Because the typical filling time of such a structure is about 100 ns and the RF source typically provides several μs long pulses, one can use a compact pulse compressor with a high compression ratio and a power gain of about 3.5 to reduce the required RF source power to only about 14 MW, which opens the door for a variety of sources, including sources that are commercially available now, and including those that include a pulse compression system.

3. Imaging and Target Position Verification Options

Given that treatment according to certain embodiments of the invention is delivered sufficiently fast to freeze physiologic motion, it is important to verify that the target is in the planned position at the time the treatment is triggered or administered. Several dynamic or "real-time" imaging or other localization technologies can be integrated into certain embodiments of the invention for this purpose. Potential such implementations can include any of the following, alone or in combination:

a. Integration of two or more x-ray fluoroscopic imaging devices, forming at least one orthogonal pair, to permit real-time 3-dimensional verification of alignment of bony anatomy and/or implanted radio-opaque fiducial markers.

b. Dynamic optical surface scanning, ideally combined with an internal imaging modality such as CT or fluoroscopy, providing real-time correlation of the external surface to the internal target position.

c. Integration of fast x-ray computed tomography. This can be accomplished by the addition of a relatively conventional multi-detector CT system within the gantry of the treatment system. Alternatively, if a continuous ring gantry design is used for the treatment delivery system, the treatment system itself can be used to scan a low energy (around 100 keV) electron beam across a ring-shaped target introduced into the beam path to produce a rapidly moving x-ray source for very fast CT scanning, known as "electron beam CT" immediately before switching to the high energy treatment beam.

d. Implantable radiofrequency beacons, whose 3-dimensional position can be read out in real time by an external antenna array. Beacons can be implanted in or near the target and serve as surrogates for the target position.

e. Integration of ultrasound. For certain anatomic locations, for example the upper abdomen and pelvis, ultrasound can provide continuous real-time 3-dimensional localization of targets.

f. While the most technologically complex to implement, magnetic resonance imaging may be implemented, which can provide real-time 3-dimensional localization of targets. Integration of MRI with conventional photon therapy systems is already commercially available or under development by multiple vendors.

In any of these implementations, dynamic visualization and/or automated image analysis tools can be used to permit either manual triggering of the treatment by the operator, or automated triggering with manual override.

4. Implementation of Intensity Modulation

According to certain embodiments of the invention, which may be used with various types of accelerators in accordance with the invention, and in order to achieve highly conformal volumetric dose shaping, radiation fields from each of multiple beam directions can cover an area with varying beam intensity across the field, with the intensity patterns optimized to produce the desired 3-dimensional dose distribution when summed across all beam directions. Such intensity modulation may be produced by raster scanning individual beamlets of varying intensity across the field from each beam direction. Alternatively, it may be produced by using a 2-dimensional intensity-modulated electron pattern at the source, effectively an array of beamlets of varying intensity, and accelerate and steer the entire array to the target volume. This eliminates the need for a raster scanning mechanism at the exit of each of the beam channels, greatly simplifying the design and reducing the bulk and cost of those components, and increases the treatment delivery speed by delivering beamlets in parallel within a much smaller number of electron pulses or bunches.

According to some embodiments, the intensity modulation of the electron source may be produced by using a photocathode illuminated by a light source with the corresponding intensity pattern, in effect, an optical image. One implementation is to use a laser as the light source, and a digital light processing (DLP) micromirror array or other intensity modulating device to produce the charge image on the photocathode to be accelerated and steered. The electron beam optics can be designed to maintain the pattern with high fidelity until it reaches the target.

Figure 8:
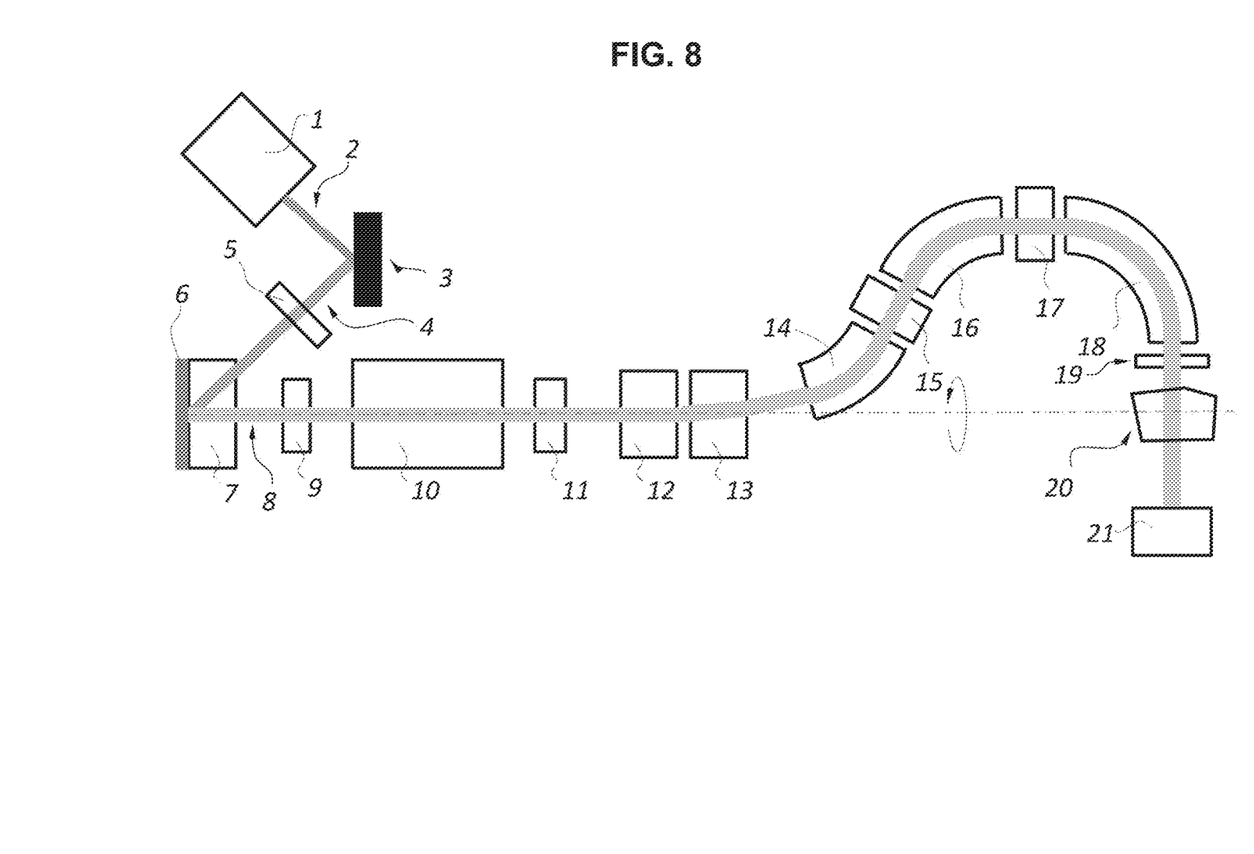
FIG. 8 schematically shows portions of a radiation treatment system with modulation of electron beam transverse profile using pulse-to-pulse modulation of injection laser beam profile impacting a photocathode of an electron injector.

According to one nonlimiting embodiment as shown in FIG. 8, a short, typically picosecond-long pulse with uniform transverse profile is generated by a laser (1). The wavelength of the laser is matched with specific photocathode material to obtain required charge and emittance. The laser pulse (2) falls on a digital-micro-mirror device (3). Pixels of this micromirror device are controlled by a computer and will reflect a portion of the laser pulse (4) thus creating an image that is then transferred to the photocathode (6) using precision projection optics (5). Although various types of accelerators may be used with this embodiment, high gradient pulsed devices with a few milliseconds between pulses are preferable. The computer modulates the mirror array thus creating a new image for each consequent pulse. A laser pulse with amplitude-modulated transverse profile that impacts the photocathode (6) will create an electron replica of the laser pulse transverse profile (8). The photocathode (6) is a part of photoelectron gun (7). The gun creates an electric field on the photocathode which accelerates the transverse-modulated electron beam. The gun also provides initial focusing for the electron beam. The electron beam then passes through the low-aberration focusing system toward accelerator (10). The accelerator increases energy of the beam to a desired value. The electron beam then passes through focusing optics (11) toward horizontal (12) and vertical (13) fast deflectors. The deflectors are controlled by a computer and are able to send the electron beam in different directions for each consecutive accelerator pulse. The desired direction will depend on (among other things) specific realization of the gantry's beam lines, number of the beam lines and whether they are movable or not. For clarity only one gantry beam line is shown in FIG. 8. After the deflectors, the electron beam passes through bending magnets (14, 16, 18) and electron optics (15, 17) and is directed through electron-beam monitoring system (19) toward the target (20). The transversely modulated electron beam irradiates the target with required distribution of the dose. After passing through the target, the beam is sent toward beam dump (21) in order to reduce unwanted radiation exposure of the target.

Of note, a greater degree of intensity modulation will produce more conformal dose distributions. However, with conventional photon therapy where intensity modulation is delivered in a serial fashion over time, more modulation comes at a cost of longer delivery time, more leakage dose to the patient, and greater uncertainty in delivered dose because of target and organ motion during the longer treatment delivery time and its interplay. With VHEE technology according to certain embodiments of the invention, all of these problems are circumvented: arbitrarily complex intensity modulation can be produced through optical imaging, and rapid parallel delivery eliminates uncertainty from interplay effects.

The concept of conversion of an optical intensity pattern into a radiation intensity pattern within a patient is considered to be unique, and also uniquely applicable to electron beam therapy in accordance with embodiments of the invention as opposed, for example, to photon or proton or other particle therapies.

E. General

Numerous specific details are set forth herein to provide a thorough understanding of the claimed subject matter. However, those skilled in the art will understand that the claimed subject matter may be practiced without these specific details. In other instances, methods, apparatuses or systems that would be known by one of ordinary skill have not been described in detail so as not to obscure subject matter that may be claimed.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed is:

1. A system for delivering very high electron energy beam to a targeted tissue in a patient, comprising:
   an accelerator capable of generating a very high electron energy beam, wherein the very high electron energy beam comprises an electron energy beam between 50 and 250 MeV;
   a beam steering device capable of receiving the very high electron energy beam from the accelerator and steering the beam to the targeted tissue from multiple directions; and
   a controller capable of controlling length of time that the very high electron energy beam irradiates the targeted tissue in delivering an entire treatment dose, the length of time of delivering the entire dose being less than 10 seconds, and to control the directions in which the beam steering device steers the beam to the targeted tissue when delivering the dose.

2. A system according to claim 1 wherein the controller is configured to receive information from an imaging or targeting device and use the information from the imaging device to control the directions in which the beam steering device steers the beam to the targeted tissue, wherein the entire is delivered to the targeted tissue by the beam steering device based on position verification data received from the imaging or targeting device.

3. A system according to claim 1 wherein the accelerator is capable of generating a beam of between 75 and 100 MeV.

4. A system according to claim 1 wherein the length of time of delivering the entire dose is less than one second.

5. A system according to claim 1 wherein the beam steering device is selected from the group consisting of electro-magnetic devices and radiofrequency deflector devices.

6. A system according to claim 1 wherein the beam steering device includes a gantry, the gantry including multiple beam ports through which the beam steering device can steer the very high electron beam received from the accelerator.

7. A system according to claim 1 wherein the beam steering device is capable of providing thin pencil beam raster scanning.

8. A system according to claim 1 wherein the beam steering device includes a continuous annular gantry.

9. A system according to claim 1 wherein the beam steering device is capable of providing volume filling scanning.

10. A system according to claim 1 wherein the beam steering device is configured to steer the very high electron energy beam from multiple directions without requiring movement of any mechanical parts.

11. A system for delivering very high electron energy beam to a targeted tissue in a patient, comprising:
an accelerator capable of generating a very high electron energy beam;
a beam steering device capable of receiving the very high electron energy beam from the accelerator and steering the beam to the targeted tissue from multiple directions;
a controller capable of controlling length of time that the very high electron energy beam irradiates the targeted tissue in delivering an entire dose of radiation to the targeted tissue, the length of time of delivering the entire dose being less than 10 seconds, and to control the directions in which the beam steering device steers the beam to the targeted tissue; and
an imaging or targeting device capable of locating the targeted tissue and providing location information to the controller configured to control the directions in which the beam steering device steers the beam to the targeted tissue.

12. A system according to claim 11 wherein the imaging or targeting device is capable of providing information to the controller of a location of the targeted tissue so as to trigger when the system delivers the beam to the targeted tissue at the location.

13. A system according to claim 11 wherein, using information from the imaging or targeting device, the system is capable of automatically delivering the beam to the targeted tissue from multiple predetermined directions at multiple predetermined points in time completing delivery of the entire dose from all directions within less than 10 seconds.

14. A system according to claim 11 wherein the accelerator is capable of generating a beam of between 75 and 100 MeV.

15. A system according to claim 11 wherein the length of time of delivery of the entire dose by irradiation of the targeted tissue with the beam is less than one second.

16. A system according to claim 11 wherein the beam steering device is selected from the group consisting of electro-magnetic devices and radiofrequency deflector devices.

17. A system according to claim 11 wherein the beam steering device is configured to steer the very high electron energy beam from multiple directions without requiring movement of any mechanical parts.

18. A method for delivering a beam of very high electron energy to a targeted tissue in a patient, comprising:
providing a system for delivering very high electron energy beam to a targeted tissue in a patient, the system comprising:
an accelerator capable of generating a very high electron energy beam;
a beam steering device capable of receiving the very high electron beam from the accelerator and steering the very high electron beam to the targeted tissue from multiple directions;
a controller capable of controlling a length of time that the very high electron beam irradiates the targeted tissue to deliver an entire treatment dose, the length of time being less than 10 seconds, and to control the directions in which the beam steering device steers the beam to the targeted tissue when delivering the dose; and
actuating the system to cause it to deliver the beam to the targeted tissue.

19. A method according to claim 18 wherein actuating the system causes a beam of between 75 and 100 MeV to be generated by the accelerator.

20. A method according to claim 18 wherein the length of time of delivery of the entire dose by irradiation of the targeted tissue with the beam is less than one second.

21. A method according to claim 18 wherein providing the system includes providing a beam steering device that is selected from the group consisting of electro-magnetic devices and radiofrequency deflector devices.

22. A method according to claim 18 wherein providing the system includes providing a beam steering device that steers the beam to the targeted tissue from multiple directions without requiring movement of any mechanical parts.

23. A method according to claim 18 further comprising providing a controller that is configured to receive information from an imaging or targeting device as to a position of the targeted tissue and use the information from the imaging or targeting device to control the directions in which the beam steering device steers the beam to the targeted tissue at the determined position and complete delivery of the entire dose before substantial movement of the targeted tissue from the determined position.

24. A method according to claim 18 further comprising providing an imaging device capable of generating images of the targeted tissue and providing information from the imaging device to the controller to control the directions in which the beam steering device steers the beam to the targeted tissue.

25. A method according to claim 24 wherein providing the imaging device includes providing an imaging device that is capable of providing information to the controller to trigger when the system delivers the beam to the targeted tissue.

26. A method according to claim 24 wherein providing the imaging device includes providing an imaging device wherein, using information from the imaging device, the system is capable of automatically delivering the beam to the targeted tissue from multiple predetermined directions concurrently or in rapid succession at multiple predetermined points in time completing delivery of the entire dose from all directions within less than 10 seconds.

27. A system for delivering a transverse-modulated electron beam to a targeted tissue in a patient, comprising:
a photoelectron gun configured to generate a transverse-modulated electron beam from an optical image produced by a light source and projected or scanned on a photocathode;
an accelerator capable of increasing the energy level of the transverse-modulated electron beam to a predetermined level;

a beam steering device capable of receiving the transverse-modulated electron beam from the accelerator and steering the transverse-modulated electron beam to the targeted tissue from multiple directions; and a controller capable of controlling length of time that the transverse-modulated electron beam irradiates the targeted tissue in delivering an entire treatment dose, the length of time being less than 10 seconds, and to control the directions in which the beam steering device steers the transverse-modulated electron beam to the targeted tissue when delivering the dose.

28. A system for delivering a transverse-modulated electron beam to a targeted tissue in a patient according to claim 27 wherein the light source is a laser.

29. A system for delivering a transverse-modulated electron beam to a targeted tissue in a patient according to claim 27, wherein the optical image comprises an intensity pattern corresponding to a dose distribution planned for delivery to the targeted tissue based on a given shape of the targeted tissue and further comprising:

an optics system capable of maintaining the intensity pattern with high fidelity during steering of the transverse-modulated beam to the targeted tissue with the beam steering device.

30. A system for delivering a transverse-modulated electron beam to a targeted tissue in a patient according to claim 27, wherein the controller is configured to:

produce a first 2-dimensional intensity pattern with the transverse-modulated electron beam with the photo-electron gun and accelerator and to steer the beam to irradiate the targeted tissue with the first 2-dimensional pattern from a first direction, and produce one or more additional 2-dimensional intensity patterns with the transverse-modulated electron beam with the photo-electron gun and accelerator and to steer the beam to irradiate the targeted tissue with the one or more additional 2-dimensional patterns from one or more additional directions, respectively, such that summing the first 2-dimensional intensity pattern and the one or more additional 2-dimensional patterns across the first direction and the one or more additional directions provides the planned dose distribution, wherein the planned dose distribution is a 3-dimensional dose distribution and the given shape is 3-dimensional.

* * * * *